(12) United States Patent
Li et al.

(10) Patent No.: US 8,269,013 B2
(45) Date of Patent: *Sep. 18, 2012

(54) SUBSTITUTED PYRAZOLE INHIBITORS OF C-MET PROTEIN KINASE

(75) Inventors: Pan Li, Lexington, MA (US); Nathan Waal, Cambridge, MA (US); Steven Ronkin, Watertown, MA (US); Qing Tang, Acton, MA (US); David Lauffer, Stow, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 152 days.

This patent is subject to a terminal disclaimer.

(21) Appl. No.: 12/788,715

(22) Filed: May 27, 2010

(65) Prior Publication Data

US 2010/0305155 A1    Dec. 2, 2010

Related U.S. Application Data

(60) Provisional application No. 61/181,784, filed on May 28, 2009.

(51) Int. Cl.
*C07D 215/12* (2006.01)
*A61K 31/47* (2006.01)

(52) U.S. Cl. ........................................ 546/176; 514/314

(58) Field of Classification Search ........................ None
See application file for complete search history.

(56) References Cited

FOREIGN PATENT DOCUMENTS

| WO | 2007064797 A2 | 6/2007 |
|---|---|---|
| WO | 2008144767 A1 | 11/2008 |
| WO | WO 2008144767 A1 * | 11/2008 |

OTHER PUBLICATIONS

PCT/US2010/036309 International Search Report.

* cited by examiner

*Primary Examiner* — Janet Andres
*Assistant Examiner* — Heidi Reese
(74) *Attorney, Agent, or Firm* — Daniel A. Pearson

(57) ABSTRACT

The present invention relates to compounds of formula I, which is useful in the inhibition of c-Met protein kinase. The invention also provides pharmaceutically acceptable compositions comprising compounds of formula I and methods of using the compositions in the treatment of proliferative disorders.

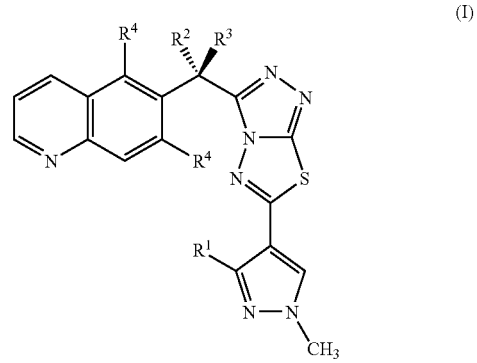

18 Claims, No Drawings

US 8,269,013 B2

SUBSTITUTED PYRAZOLE INHIBITORS OF C-MET PROTEIN KINASE

This present application claims the benefit, under 35 U.S.C. §119, to U.S. Provisional Application No. 61/181,784, filed May 28, 2009 the entire disclosure of which is incorporated herein by reference.

TECHNICAL FIELD OF THE INVENTION

The present invention relates to selective inhibitors of c-Met. The invention also provides pharmaceutically acceptable compositions comprising a c-Met inhibitor and methods of using the compositions in the treatment of various proliferative disorders.

BACKGROUND OF THE INVENTION

Hepatocyte growth factor (HGF), also known as scatter factor, is a multi-functional growth factor that enhances transformation and tumor development by inducing mitogenesis and cell motility. Further, HGF promotes metastasis by stimulating cell motility and invasion through various signaling pathways. In order to produce cellular effects, HGF must bind to its receptor, c-Met, a receptor tyrosine kinase, c-Met, a widely expressed heterodimeric protein comprising of a 50 kilodalton (kDa) α-subunit and a 145 kDa alpha-subunit (Maggiora et al., *J. Cell Physiol.*, 173:183-186, 1997), is overexpressed in a significant percentage of human cancers and is amplified during the transition between primary tumors and metastasis. The various cancers in which c-Met overexpression is implicated include, but are not limited to, gastric adenocarcinoma, renal cancer, small cell lung carcinoma, colorectal cancer, prostate cancer, brain cancer, liver cancer, pancreatic cancer, and breast cancer, c-Met is also implicated in atherosclerosis and lung fibrosis.

Accordingly, there is a great need to develop compounds useful as inhibitors of c-Met protein kinase receptor. In particular, preferred compounds should have high affinity to the c-Met receptor and show functional activity as antagonists, while showing little affinity for other kinase receptors.

SUMMARY OF THE INVENTION

It has been found that 1-methyl-1H-pyrazol-4-yl-[1,2,4]triazolo[3,4-b][1,3,4]thiadiazol-3-yl)methyl)quinolines that are substituted at the pyrazole 3-position, and optionally substituted on the methylene group linking the triazolothiadiazole and quinoline rings, are effective in the inhibition of c-Met.

Accordingly, the invention features a compound having the formula:

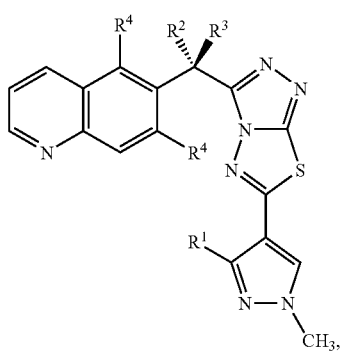

or a pharmaceutically acceptable salt thereof, wherein each of $R^1$, $R^2$, $R^3$, and $R^4$ are as defined elsewhere herein.

The invention also provides pharmaceutical compositions that include a compound of formula I and a pharmaceutically acceptable carrier, adjuvant, or vehicle. In addition, the invention provides methods of treating or lessening the severity of a proliferative disease, condition, or disorder in a patient that includes the step of administering to the patient a therapeutically effective dose of a compound of formula I, or a pharmaceutical composition thereof.

DETAILED DESCRIPTION OF THE INVENTION

Definitions and General Terminology

As used herein, the following definitions shall apply unless otherwise indicated. For purposes of this invention, the chemical elements are identified in accordance with the Periodic Table of the Elements, CAS version, and the Handbook of Chemistry and Physics, $75^{th}$ Ed. 1994. Additionally, general principles of organic chemistry are described in "Organic Chemistry," Thomas Sorrell, University Science Books, Sausalito: 1999, and "March's Advanced Organic Chemistry," $5^{th}$ Ed., Smith, M. B. and March, J., eds. John Wiley & Sons, New York: 2001, the entire contents of which are hereby incorporated by reference.

Description of the Compound of the Invention

In a first aspect, the invention features the following compounds of formula I:

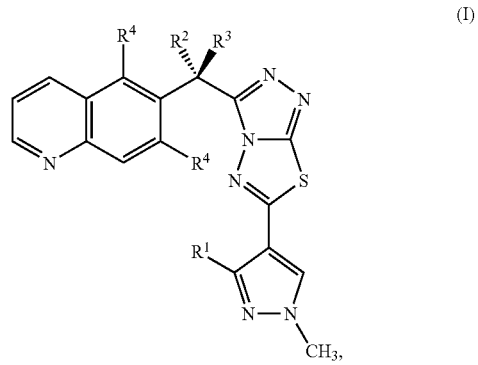

or pharmaceutically acceptable salts thereof, wherein $R^1$ is cyclopropyl or $C_{1-3}$ aliphatic, optionally substituted with 1-3 fluorine atoms; $R^2$ is hydrogen, fluoro, or methyl; $R^3$ is hydrogen, fluoro, or methyl; and each $R^4$ is, independently, hydrogen or fluoro.

In one embodiment, $R^1$ is methyl, ethyl, trifluoromethyl, isopropyl, or cyclopropyl; $R^2$ is hydrogen or methyl; $R^3$ is hydrogen or methyl; and $R^4$ is hydrogen or fluoro. In another embodiment, $R^1$ is methyl, ethyl, trifluoromethyl, isopropyl, or cyclopropyl; each of $R^2$ and $R^3$ is fluoro; and $R^4$ is hydrogen.

In one embodiment, $R^1$ is methyl.
In another embodiment, $R^1$ is ethyl, trifluoromethyl, isopropyl, or cyclopropyl
In one embodiment, $R^2$ is hydrogen and $R^3$ is methyl.
In another embodiment, $R^2$ is methyl and $R^3$ is hydrogen.
In another embodiment, each of $R^2$ and $R^3$ is fluoro.
In yet another embodiment, each of $R^2$ and $R^3$ is hydrogen.
In one embodiment, each of $R^4$ is hydrogen.
In another embodiment, each of $R^4$ is fluoro.

Compounds of formula I include the following:
1
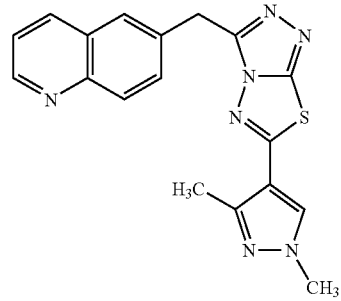
2
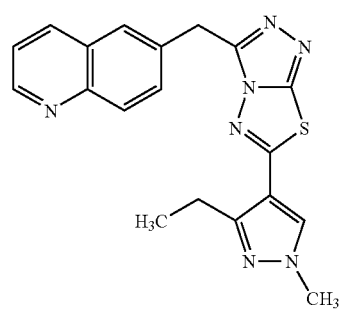
3
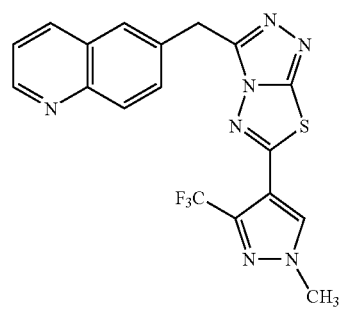
4
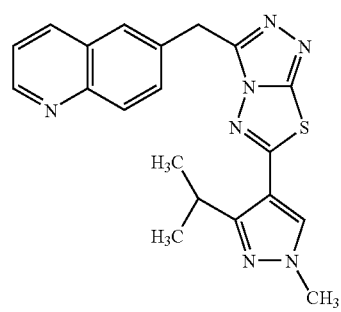
5
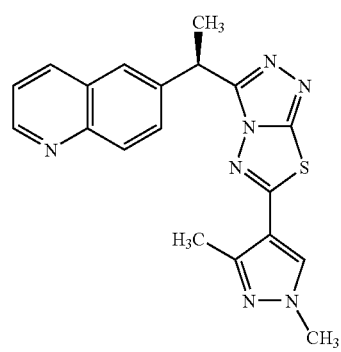
6
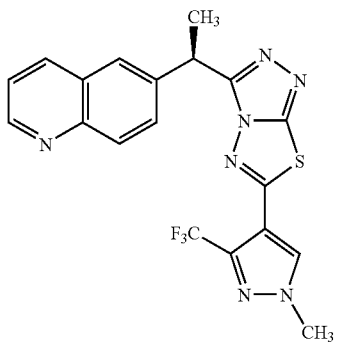
7
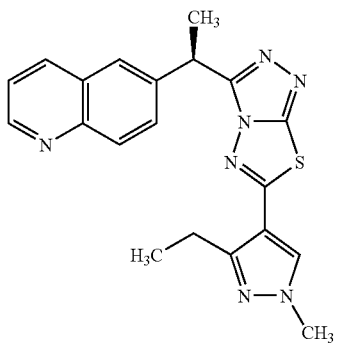
8
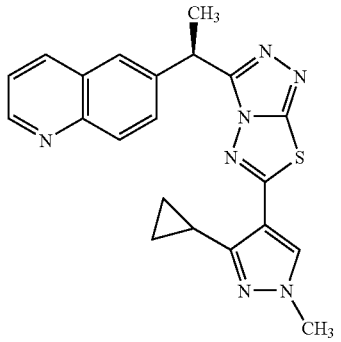
9
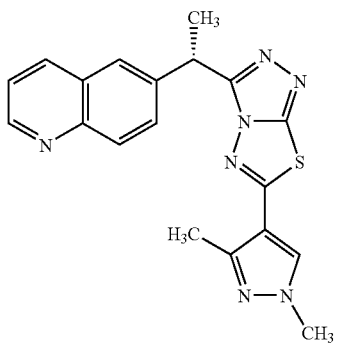

-continued
10
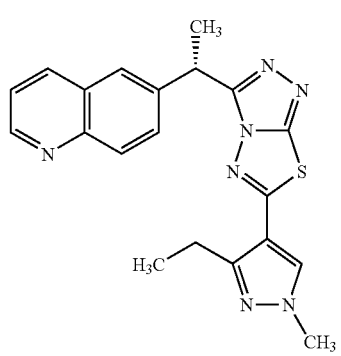
11
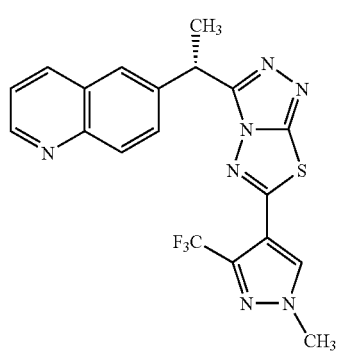
12
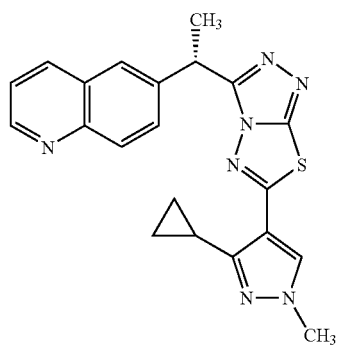
13
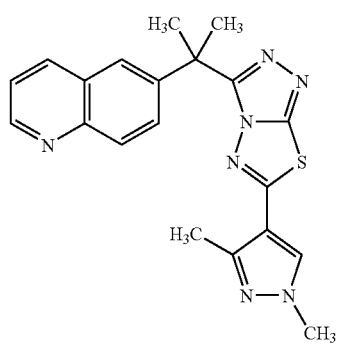
-continued
14
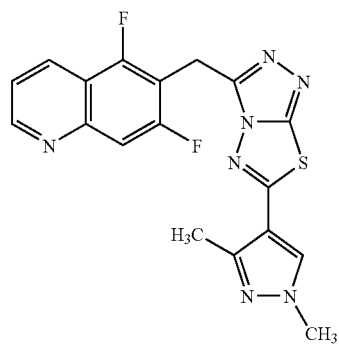
15
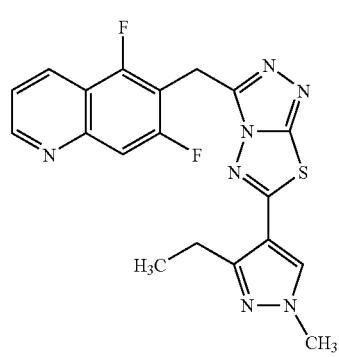
16
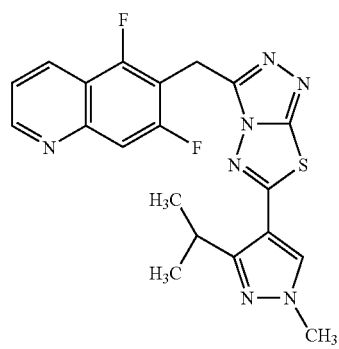
17
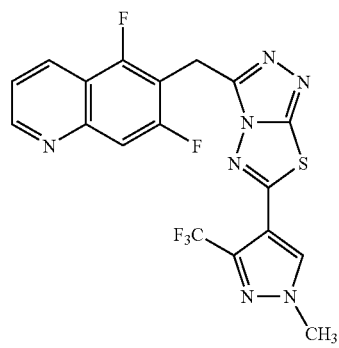

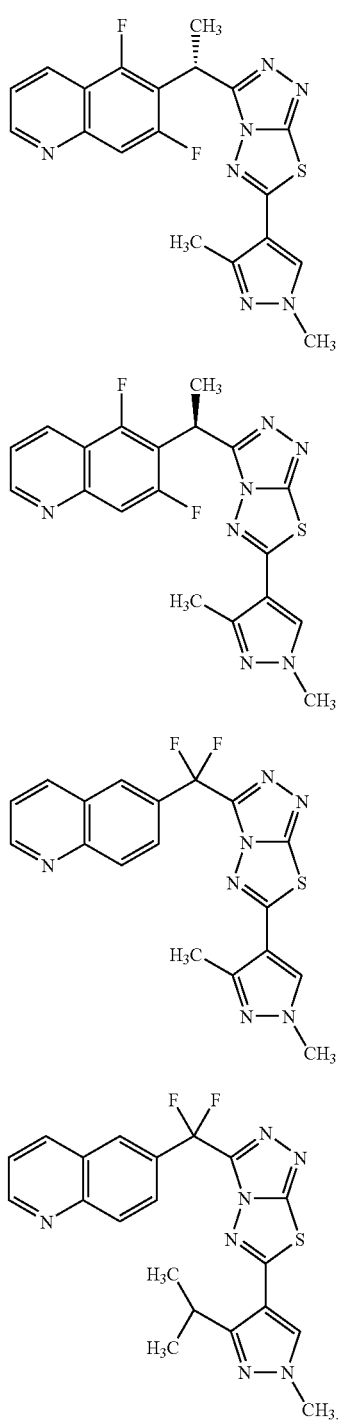

In another aspect, the invention features a pharmaceutical composition comprising a compound of formula I, or a pharmaceutically acceptable salt thereof, and a pharmaceutically acceptable carrier, adjuvant or vehicle. In one embodiment, the composition includes an additional chemotherapeutic or anti-proliferative agent, an anti-inflammatory agent, an agent for treating atherosclerosis, or an agent for treating lung fibrosis.

In another aspect, the invention features a method of treating or lessening the severity of a proliferative disorder in a patient comprising administering a compound of formula I in an amount sufficient to treat or lessen the severity of a proliferative disorder in said patient. In one embodiment, the proliferative disorder is metastatic cancer. In another embodiment, the proliferative disorder is a glioblastoma; hepatocellular carcinoma, a gastric carcinoma; or a cancer selected from colon, breast, prostate, brain, liver, pancreatic or lung cancer.

Compositions, Formulations, and Administration of Compounds of the Invention

In another aspect, the invention provides a composition comprising a compound of formula I or a pharmaceutically acceptable derivative thereof and a pharmaceutically acceptable carrier, adjuvant, or vehicle. In one embodiment, the amount of compound in a composition of this invention is such that is effective to measurably inhibit c-Met in a biological sample or in a patient. Preferably the composition of this invention is formulated for administration to a patient in need of such composition. Most preferably, the composition of this invention is formulated for oral administration to a patient.

The term "patient", as used herein, means an animal, preferably a mammal, and most preferably a human.

It will also be appreciated that the compounds of formula I can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound of formula I as otherwise described herein, or a metabolite or residue thereof.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of compounds of formula I include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\text{ alkyl})_4$ salts.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy,* 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with a compound of formula I, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of compounds of formula I include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of formula I, it is often desirable to slow the absorption of this compound from subcutaneous or intramuscular injection. This may be accomplished by the use of a liquid suspension of crystalline or amorphous material with poor water solubility. The rate of absorption of a compound of formula I then depends upon its rate of dissolution that, in turn, may depend upon crystal size and crystalline form. Alternatively, dissolving or suspending a compound of formula I in an oil vehicle accomplishes delayed absorption of a parenterally administered compound form. Injectable depot forms are made by forming microencapsule matrices of a compound of formula I in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping a compound of formula I in liposomes or microemulsions that are compatible with body tissues.

Compositions for rectal or vaginal administration are preferably suppositories which can be prepared by mixing a compound of formula I with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of formula I include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound of formula I to the body. Such dosage forms can be made by dissolving or dispensing a compound of formula I in the proper medium. Absorption enhancers can also be used to increase the flux of a compound of formula I across the skin. The rate can be controlled by either providing a rate controlling membrane or by dispersing a compound of formula I in a polymer matrix or gel.

Compounds of formula I are preferably formulated in dosage unit form for ease of administration and uniformity of dosage. The expression "dosage unit form" as used herein refers to a physically discrete unit of agent appropriate for the patient to be treated. It will be understood, however, that the total daily usage of a compound of formula I and compositions comprising a compound of formula I will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of a compound of formula I that may be combined with the carrier materials to produce a composition in a single dosage form will vary depending upon the host treated, the particular mode of administration. Preferably, the compositions should be formulated so that a dosage of from 0.01 to 100 mg/kg body weight/day of the inhibitor can be administered to a patient receiving these compositions. In one example, compositions are formulated such that the dosage of a compound of formula I is from 5 to 30 mg/kg body weight/day.

Depending upon the particular condition, or disease, to be treated or prevented, additional therapeutic agents, which are normally administered to treat or prevent that condition, may also be present in the compositions of this invention. As used herein, additional therapeutic agents that are normally administered to treat or prevent a particular disease, or condition, are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of Compounds of Formula I and Compositions Comprising Compounds of Formula I According to one embodiment, the invention relates to a method of inhibiting c-Met protein kinase activity in a biological sample comprising the step of contacting said biological sample with a compound of formula I, or a composition comprising said compound. The term "biological sample," as used herein, means a sample outside a living organism and includes, without limitation, cell cultures or extracts thereof biopsied material obtained from a mammal or extracts thereof and blood, saliva, urine, feces, semen, tears, or other body fluids or extracts thereof. Inhibition of kinase activity in a biological sample is useful for a variety of purposes known to one of skill in the art. Examples of such purposes include, but are not limited to, biological specimen storage and biological assays. In one embodiment, the method of inhibiting kinase activity in a biological sample is limited to non-therapeutic methods.

The term "c-Met" is synonymous with "c-MET," "cMet", "MET", "Met" or other designations known to one skilled in the art.

According to another embodiment, the invention relates to a method of inhibiting c-Met kinase activity in a patient comprising the step of administering to said patient a compound of formula I, or a composition comprising said compound.

The term "c-Met-mediated disease" or "c-Met-mediated condition", as used herein, means any disease state or other deleterious condition in which c-Met is known to play a role. The terms "c-Met-mediated disease" or "c-Met-mediated condition" also mean those diseases or conditions that are alleviated by treatment with a c-Met inhibitor. Such conditions include, without limitation, renal, gastric, colon, brain, breast, prostate, liver, pancreatic, or lung cancer, glioblastoma, atherosclerosis, or lung fibrosis.

In one aspect, the present invention features a method treating a proliferative disorder in a patient comprising the step of administering to the patient a therapeutically effective dose of a compound of formula I or a composition comprising a compound of formula I.

According to one embodiment, the proliferative disorder is cancer, such as, for example, renal, gastric, colon, brain, breast, liver, prostate, and lung cancer, or a glioblastoma.

In another embodiment, the present invention relates to a method of treating or lessening the severity of hepatocellular carcinoma in a patient in need thereof, comprising administering to said patient a compound of formula I or composition thereof.

In another embodiment, the proliferative disorder is polycythemia vera, essential thrombocythemia, chronic idiopathic myelofibrosis, myeloid metaplasia with myelofibrosis, chronic myeloid leukemia (CML), chronic myelomonocytic leukemia, chronic eosinophilic leukemia, hypereosinophilic syndrome, systematic mast cell disease, atypical CML, or juvenile myelomonocytic leukemia.

In another embodiment, the proliferative disorder is atherosclerosis or lung fibrosis.

Another aspect of the present invention relates to a method of inhibiting tumor metastasis in a patient in need thereof, comprising administering to said patient a compound of formula I or a composition thereof.

Depending upon the particular condition, or disease, to be treated, additional therapeutic agents that are normally administered to treat that condition may also be present in the compositions of this invention. As used herein, additional therapeutic agents that are normally administered to treat a particular disease, or condition, are known as "appropriate for the disease, or condition, being treated".

In one embodiment, chemotherapeutic agents or other antiproliferative agents may be combined with a compound of formula I to treat proliferative diseases and cancer. Examples of known chemotherapeutic agents include, but are not limited to, alkylating agents, such as, for example, cyclophosphamide, lomustine, busulfan procarbazine, ifosfamide, altretamine, melphalan, estramustine phosphate, hexamethylmelamine, mechlorethamine, thiotepa, streptozocin, chlorambucil, temozolomide, dacarbazine, semustine, or carmustine; platinum agents, such as, for example, cisplatin, carboplatinum, oxaliplatin, ZD-0473 (AnorMED), spiroplatinum, lobaplatin (Aeterna), carboxyphthalatoplatinum, satraplatin (Johnson Matthey), tetraplatin BBR-3464, (Hoffmann-La Roche), ormiplatin, SM-11355 (Sumitomo), iproplatin, or AP-5280 (Access); antimetabolites, such as, for example, azacytidine, tomudex, gemcitabine, trimetrexate, capecitabine, deoxycoformycin, 5-fluorouracil, fludarabine, floxuridine, pentostatin, 2-chlorodeoxyadenosine, raltitrexed, 6-mercaptopurine, hydroxyurea, 6-thioguanine, decitabine (SuperGen), cytarabin, clofarabine (Bioenvision), 2-fluorodeoxy cytidine, irofulven (MGI Pharma), methotrexate, DMDC (Hoffmann-La Roche), idatrexate, or ethynylcytidine (Taiho); topoisomerase inhibitors, such as, for example, amsacrine, rubitecan (SuperGen), epirubicin, exatecan mesylate (Daiichi), etoposide, quinamed (ChemGenex), teniposide, mitoxantrone, gimatecan (Sigma-Tau), irinotecan (CPT-11), diflomotecan (Beaufour-Ipsen), 7-ethyl-10-hydroxy-camptothecin, TAS-103 (Taiho), topotecan, elsamitrucin (Spectrum), dexrazoxanet (TopoTarget), J-107088 (Merck & Co), pixantrone (Novuspharma), BNP-1350 (BioNumerik), rebeccamycin analogue (Exelixis), CKD-602 (Chong Kun Dang), BBR-3576 (Novuspharma), or KW-2170 (Kyowa Hakko); antitumor antibiotics, such as, for example, dactinomycin (actinomycin D), amonafide, doxorubicin (adriamycin), azonafide, deoxyrubicin, anthrapyrazole, valrubicin, oxantrazole, daunorubicin (daunomycin), losoxantrone, epirubicin, bleomycin, sulfate (blenoxane), therarubicin, bleomycinic acid, idarubicin, bleomycin A, rubidazone, bleomycin B, plicamycin, mitomycin C, porfiromycin, MEN-10755 (Menarini), cyanomorpholinodoxorubicin, GPX-100 (Gem Pharmaceuticals), or mitoxantrone (novantrone), antimitotic agents, such as, for example, paclitaxel, SB 408075 (GlaxoSmithKline), docetaxel, E7010 (Abbott), colchicines, PG-TXL (Cell Therapeutics), vinblastine, IDN 5109 (Bayer), vincristine A, 105972 (Abbott), vinorelbine, A 204197 (Abbott), vindesine, LU 223651 (BASF), dolastatin 10 (NCI), D 24851 (ASTAMedica), rhizoxin (Fujisawa), ER-86526 (Eisai), mivobulin (Warner-Lambert), combretastatin A4 (BMS), cemadotin (BASF), isohomohalichondrin-B (PharmaMar), RPR 109881A (Aventis), ZD 6126 (AstraZeneca), TXD 258 (Aventis), PEG-paclitaxel (Enzon,) epothilone B (Novartis), AZ10992 (Asahi), T 900607 (Tularik), IDN-5109 (Indena), T 138067 (Tularik), AVLB (Prescient NeuroPharma), cryptophycin 52 (Eli Lilly), azaepothilone B (BMS), vinflunine (Fabre), BNP-7787 (BioNumerik), auristatin PE (Teikoku Hormone), CA-4 prodrug (OXiGENE), BMS 247550 (BMS), dolastatin-10 (NIH), BMS 184476 (BMS), CA-4 (OXiGENE), BMS 188797 (BMS), or taxoprexin (Protarga); aromatase inhibitors, such as, for example, aminoglutethimide, exemestane, letrozole, atamestane (BioMedicines), anastrazole, YM-511 (Yamanouchi), or formestane; thymidylate synthase inhibitors, such as, for example, pemetrexed (Eli Lilly), nolatrexed (Eximias), ZD-9331 (BTG), or CoFactor™ (BioKeys); DNA antagonists, such as, for example, trabectedin (PharmaMar), mafosfamide (Baxter International), glufosfamide (Baxter International), apaziquone (Spectrum Pharmaceuticals), albumin+$^{32}$P (Isotope Solutions), O6 benzyl guanine (Paligent), thymectacin (NewBiotics), or edotreotide (Novartis); farnesyltransferase inhibitors, such as, for example, arglabin (NuOncology Labs), tipifarnib (Johnson & Johnson), lonafarnib (Schering-Plough), perillyl alcohol (DOR BioPharma), or BAY-43-9006 (Bayer); Pump inhibitors, such as, for example, CBT-1 (CBA Pharma), zosuquidar trihydrochloride (Eli Lilly), tariquidar (Xenova), biricodar dicitrate (Vertex), or MS-209 (Schering AG); Histone acetyltransferase inhibitors, such as, for example, tacedinaline (Pfizer), pivaloyloxymethyl butyrate (Titan), SAHA (Aton Pharma), depsipeptide (Fujisawa), or MS-275 (Schering AG); Metalloproteinase inhibitors, such as, for example, Neovastat (Aeterna Laboratories), CMT-3 (CollaGenex), marimastat (British Biotech), or BMS-275291 (Celltech); ribonucleoside reductase inhibitors, such as, for example, gallium maltolate (Titan), tezacitabine (Aventis), triapine (Vion), or didox (Molecules for Health); TNF alpha agonists/antagonists, such as, for example, virulizin (Lorus Therapeutics), revimid (Celgene), CDC-394 (Celgene), entanercept (Immunex Corp.), infliximab (Centocor, Inc.), or adalimumab (Abbott Laboratories); endothelin A receptor antagonists, such as, for example, atrasentan (Abbott) YM-598 (Yamanouchi) or ZD-4054 (AstraZeneca); retinoic acid receptor agonists, such as, for example, fenretinide (Johnson & Johnson) alitretinoin (Ligand) or LGD-1550 (Ligand); immuno-modulators, such as, for example, interferon dexosome therapy (Anosys), oncophage (Antigenics), pentrix (Australian Cancer Technology), GMK (Progenics), ISF-154 (Tragen), adenocarcinoma vaccine (Biomira), cancer vaccine (Intercell), CTP-37 (AVI BioPharma), norelin (Biostar), IRX-2 (Immuno-Rx), BLP-25 (Biomira), PEP-005 (Peplin Biotech), MGV (Progenics), synchrovax vaccines (CTL Immuno), beta-alethine (Dovetail), melanoma vaccine (CTL Immuno), CLL therapy (Vasogen), or p21 RAS vaccine (GemVax); hormonal and antihormonal agents, such as, for example, estrogens, prednisone, conjugated estrogens, methylprednisolone, ethinyl estradiol, prednisolone, chlortrianisen, aminoglutethimide, idenestrol, leuprolide, hydroxyprogesterone caproate, goserelin, medroxyprogesterone, leuporelin, testosterone, bicalutamide, testosterone propionate, fluoxymesterone, flutamide, methyltestosterone, octreotide, diethylstilbestrol, nilutamide, megestrol, mitotane, tamoxifen, P-04 (Novogen), toremofine, 2-methoxyestradiol (EntreMed), dexamethasone, or arzoxifene (Eli Lilly); photodynamic agents, such as, for example, talaporfin (Light Sciences), Pd-bacteriopheophorbide (Yeda), Theralux (Theratechnologies), lutetium texaphyrin (Pharmacyclics), motexafin gadolinium (Pharmacyclics), or hypericin; and tyrosine kinase inhibitors, such as, for example, imatinib (Novartis), kahalide F (PharmaMar), leflunomide (Sugen/Pharmacia), CEP-701 (Cephalon), ZD1839 (AstraZeneca), CEP-751 (Cephalon), erlotinib (Oncogene Science), MLN518 (Millenium), canertinib (Pfizer), PKC412 (Novartis), squalamine (Genaera), phenoxodiol, SU5416 (Pharmacia), trastuzumab (Genentech), SU6668 (Pharmacia), C225 (ImClone), ZD4190 (AstraZeneca), rhu-Mab (Genentech), ZD6474 (AstraZeneca), MDX-H210 (Medarex), vatalanib (Novartis), 2C4 (Genentech), PKI166 (Novartis), MDX-447 (Medarex), GW2016 (GlaxoSmithKline), ABX-EGF (Abgenix), EKB-509 (Wyeth), IMC-1C11 (ImClone), or EKB-569 (Wyeth).

Those additional agents may be administered separately from the a compound of formula I-containing composition, as part of a multiple dosage regimen. Alternatively, those agents may be part of a single dosage form, mixed together with a compound of formula I in a single composition. If administered as part of a multiple dosage regime, the two active agents may be submitted simultaneously, sequentially or within a period of time from one another normally within five hours from one another.

The amount of both, a compound of formula I and the additional therapeutic agent (in those compositions which comprise an additional therapeutic agent as described above)) that may be combined with the carrier materials to produce a single dosage form will vary depending upon the host treated and the particular mode of administration. Preferably, the compositions of this invention should be formulated so that a dosage of between 0.01-100 mg/kg body weight/day of a compound of formula I can be administered. In one example, compositions are formulated such that the dosage of a compound of formula I is from 3 to 30 mg/kg body weight/day.

In those compositions that comprise an additional therapeutic agent, that additional therapeutic agent and a compound of formula I may act synergistically. Therefore, the amount of additional therapeutic agent in such compositions will be less than that required in a monotherapy utilizing only that therapeutic agent. In such compositions a dosage of between 0.01-100 mg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Compounds of formula I, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition. Implantable devices coated with a compound of formula I are another embodiment of the present invention.

In order that the invention described herein may be more fully understood, the following examples are set forth. It should be understood that these examples are for illustrative purposes only and are not to be construed as limiting this invention in any manner.

Preparation of Compound 1

The following definitions describe terms and abbreviations used herein:
Brine a saturated solution of NaCl in water
BSA bovine serum albumin
DMSO dimethylsulfoxide
ESMS electrospray mass spectrometry
EtOAc ethyl acetate
EtOH ethyl alcohol
HPLC high performance liquid chromatography
LCMS liquid chromatography-mass spectrometry
Me methyl
MeOH methanol
Ph phenyl
RT room temperature
TCA trichloroacetic acid
THF tetrahydrofuran
TFA trifluoacetic acid As used herein, other abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997, herein incorporated in its entirety by reference.

As used herein, the term "$R_t$(min)" refers to the HPLC retention time, in minutes, associated with a compound. Unless otherwise indicated, the HPLC method utilized to obtain the reported retention time is as follows: column: Zorbax SB C18 column, 3.0×150 mm; gradient: 10-90% acetonitrile/water (0.1% TFA), 5 minutes; flow rate: 1.0 mL/minute; and detection: 254 & 214 nm.

Preparation of the Compounds of the Invention

Example 1

Compounds of Formula II

Compounds 1001 and 1002 were purchased from Okeanos Tech, Beijing, China (Catalog Nos. OK-J-05024 and OK-J-05025, respectively). Compound 1003 was prepared from compound 1002 by (i) preparing the methyl ester, (ii) treating the methyl ester with lithium diisopropylamide, followed by treatment with methyl iodide, and (iii) hydrolysis of the α,α-dimethyl methyl ester to the carboxylic acid.

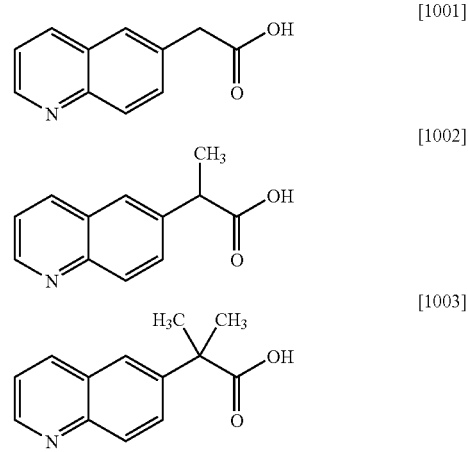

Compound 1004 was prepared as shown in Scheme 1. Accordingly, as shown in step 1-i, to a suspension of NaH (60% in mineral oil, 8.47 g, 212 mmol) in DMSO at 0° C. (260 mL) was slowly added diethyl 2-methylmalonate (compound 1005, 29.5 g, 169.4 mmol). The mixture was stirred at 0° C. for 2 hours and 3,4,5-trifluoronitrobenzene (25 g, 141.2 mmol) was added. The resulting mixture was warmed to RT and stirred for 12 hours. The reaction mixture was poured into saturated aq. NH₄Cl solution and the precipitate was collected by filtration. After washing with water 3 times, the resulting diethyl 2-(2,6-difluoro-4-nitrophenyl)-2-methylmalonate (compound 1006 [R=CH₃], 44.5 g, 95% yield) was dried under reduced pressure and used as is in the next reaction.

As shown in step 1-ii, to a solution of diethyl 2-(2,6-difluoro-4-nitro-phenyl)-2-methylmalonate (44.5 g, 135 mmol) in MeOH was added Pd/C (10%, 4.0 g) under an atmosphere of nitrogen. The atmosphere was replaced with H₂ and the mixture hydrogenated at 50 psi for 3 days. The atmosphere was replaced with nitrogen, the mixture filtered through diatomaceous earth, and the volatiles removed under reduced pressure. The resulting diethyl 2-(4-amino-2,6-difluorophenyl)-2-methylmalonate (compound 1007 [R=CH₃], 40.5 g, 99% yield) was dried under reduced pressure and used as is in the next reaction.

As shown in step 1-iii, to a solution of diethyl 2-(4-amino-2,6-difluorophenyl)-2-methylmalonate (40.0 g, 132.8 mmol) in methanol (200 mL) was added 6M NaOH (110.7 mL, 664.0 mmol). The mixture was heated at 100° C. for 4 hours, cooled to 0° C., and acidified with conc. HCl until a pH of 3 was obtained. The mixture was warmed to RT and stirred for 3 hours. The resulting precipitate was collected by filtration, washed with water, and dried under high vacuum at 50° C. for 20 hours to provide 2-(4-amino-2,6-difluorophenyl)propanoic acid (compound 1008 [R=CH₃], 22 g, 84% yield): $^1$H NMR (300.0 MHz, DMSO) δ 12.25 (brs, 1H), 6.16 (d, J=10.8 Hz, 2H), 5.58 (s, 2H), 3.74 (q, J=7.2 Hz, 1H) and 1.28 (d, J=7.2 Hz, 3H) ppm.

As shown in step 1-iv, a mixture of 2-(4-amino-2,6-difluorophenyl)propanoic acid (19.0 g, 94.45 mmol), glycerol (35.83 g, 28.41 mL, 389.1 mmol), nitrobenzene (7.209 g, 6.028 mL, 58.56 mmol) and concentrated sulfuric acid (30.57 g, 16.61 mL, 311.7 mmol) was heated gently. After cessation of the initial vigorous reaction, the mixture was heated to 170° C. for 16 hours. After cooling, the volatiles were removed under reduced pressure, the residue dissolved in MeOH (150 mL), 150 mL of 6N NaOH were added, and the mixture was heated at 110° C. for 3 hours. After cooling to RT, the mixture was acidified with concentrated HCl to a pH of 3. The resulting dark precipitate was collected by filtration and washed with water. The precipitate was taken up in ethanol and thionyl chloride (11.24 g, 6.891 mL, 94.45 mmol) was carefully added dropwise. After addition was complete, the mixture was heated at 50° C. for 20 hours. After cooling to RT, the volatiles were removed under reduced pressure and the residue was dissolved in a mixture of sat'd NaHCO₃ and DCM. The layers were separated and the aqueous layer extracted with DCM. The combined organics were dried over MgSO4, reduced in volume under reduced pressure, and subjected to medium-pressure silica gel chromatography (0% EtOAc/Hexanes to 30% in 36 minutes) to provide methyl 2-(5,7-difluoroquinolin-6-yl)propanoate (14.0 g, 56% yield for two steps). The methyl ester (5.0 g) was saponified by taking it up in methanol (30 mL), treating the resulting solution with NaOH (16.58 mL of 6 M, 99.50 mmol), and stirring at RT for 20 hours. After careful acidification with conc. HCl to a pH of 2, the resulting precipitate was collected by filtration and dried under high vacuum to provide 2-(5,7-difluoroquinolin-6-yl)propanoic acid, which was used as is in subsequent reactions. Compound 1003 can be prepared by the same procedure as used in the preparation of compound 1004 by replacing-diethyl 2-methylmalonate with diethyl malonate.

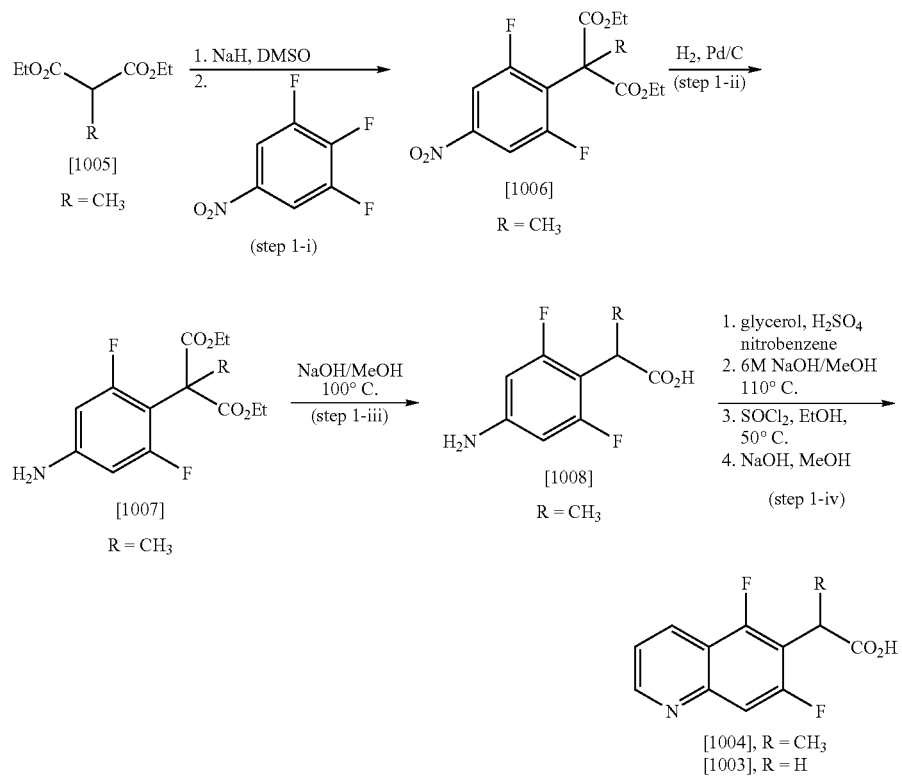

Example 2

Preparation of Compounds of Formula III

Compounds of formula III, wherein $R^2$ and $R^3$ are hydrogen or methyl, can be prepared as shown in Scheme 2. Accordingly, as shown in step 2-i of Scheme 2, the appropriately substituted quinoline acetic acid of formula II (248.5 mmol, 1.0 equivalent) and 1,3-diaminothiourea (273.4 mmol, 1.1 equivalents) is suspended in a mixture of tetramethylene sulfone (sulfolane, 38 mL) and water (57 mL). Methane sulfonic acid (546.7 mmol, 2.2 equivalents) is added to the mixture, whereupon all solids dissolve. The reaction mixture is slowly warmed to 90° C. and the reaction heated at 90° C. for 40 hours. The reaction mixture is cooled in an ice bath and water (75 mL) is added, followed by the careful addition of saturated sodium bicarbonate (500 mL) until a pH 8 is achieved. The resulting precipitate is collected by vacuum filtration, washed with water, saturated sodium bicarbonate, water, and methyl t-butyl ether, respectively. The product is dried in a vacuum oven at 55° C. to afford a compound of formula III.

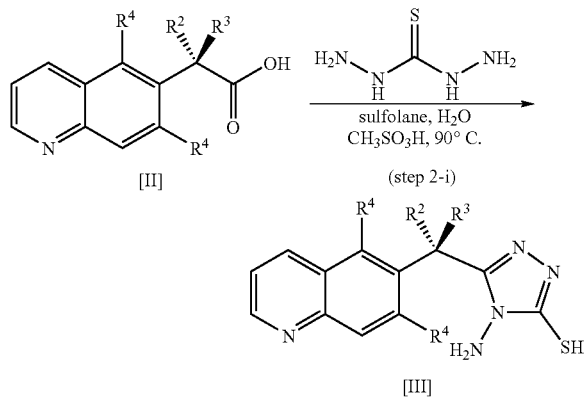

Example 3

Preparation of 5-(difluoro(quinolin-6-yl)methyl)-4-amino-4H-1,2,4-triazole-3-thiol (Compound 1010)

Compounds of Formula III, wherein each of $R^2$ and $R^3$ is fluoro and $R^4$ is hydrogen, can be prepared as shown in Scheme 3. Accordingly, as shown in step 3-i, to a mixture of 6-iodoquinoline (10.0 g, 39.21 mmol, purchased from Hangzhou Trylead Chemical Technology Co., Ltd., China) and copper (nanopowder) (9.964 g, 156.8 mmol) in DMSO (150 mL) was added ethyl 2-bromo-2,2-difluoro-acetate (10.35 g, 50.97 mmol). The mixture was heated at 60° C. for 6 h, during which time the mixture turned from red copper suspension into a dark red near-homogenous solution. After cooling to room temperature, the mixture was diluted with ethyl acetate (300 mL) and aq saturated NH$_4$Cl solution (450 mL). After stirring for 30 minutes, the organic layer was separated, washed with water, washed with brine, and dried over magnisium sulfate. Removal of the volatiles under reduced pressure give crude product as red liquid. Purification by medium pressure silica gel chromatography (DCM/ethyl acetate: 100% to 30% in 25 min.) gave ethyl 2,2-difluoro-2-(quinolin-6-yl)acetate (compound 1009, 51% yield): $^1$H NMR (300.0 MHz, CDCl$_3$) δ 9.04-9.03 (m, 1H), 8.29-8.21 (m, 2H), 8.15 (s, 1H), 7.93 (dd, J=2.1, 8.9 Hz, 1H), 7.52 (q, J=4.2 Hz, 1H), 4.35 (q, J=7.1 Hz, 2H) and 1.34 (t, J=7.1 Hz, 3H) ppm.

As shown in step 3-ii in Scheme 3, compound 1009 (10.0 g, 39.80 mmol) was dissolved in ethanol (100 mL), hydrazine (7.65 g, 7.50 mL, 239 mmol) was added, and the reaction mixture was stirred at room temperature for 10 minutes. After pouring the mixture into 2N HCl solution, the aqueous mixture was washed twice with DCM and the pH was adjusted to 8 while bubbling nitrogen gas through the solution. The resulting aqueous solution was exhaustively extracted with DCM (10×) and the combined organics dried over MgSO4, filtered, and the volatiles removed under reduced pressure to provide 2,2-difluoro-2-(quinolin-6-yl)acetohydrazide as a yellow solid (compound 1010, 91% yield). This compound that was used directly without further purification.

As shown in step 3-iii of Scheme 3, compound 1010 (3.55 g, 14.97 mmol) in EtOH (71 mL) was treated with potassium hydroxide (924 mg, 16.5 mmol) and the reaction mixture gently warmed to achieve homogeneity. Carbon disulfide (1.38 g, 1.09 mL, 18.2 mmol) was added and the mixture stirred at 90° C. for 4 hours, at which time intermediate compound 5-(difluoro(quinolin-6-yl)methyl)-1,3,4-oxadiazole-2-thiol, sodium salt was formed. To the refluxing solution was added hydrazine (4.80 g, 4.70 mL, 150 mmol), followed by addition of 3A molecular sieves (3 g). After refluxing for 2 hours, the sieves were removed by filtration and washed with EtOH. The combined organics were cooled to 0° C. in an ice bath and treated with conc. HCl under an atmosphere of nitrogen until a pH of 6.5 was achieved. The precipitate was removed by filtration and the filtrate refluxed for 4 hours, using a Dean-Stark trap to collect any excess water. The volatiles were removed under reduced pressure, the residue taken up to water, and the pH adjusted to 6.5. The resulting solid was collected by filtration, washed with water, and dried to produce 5-(difluoro(quinolin-6-yl)methyl)-4-amino-4H-1,2,4-triazole-3-thiol (compound 1011, 61% yield): $^1$H NMR (300.0 MHz, DMSO) δ 14.28 (s, 1H), 9.03-9.02 (m, 1H), 8.56 (d, J=8.0 Hz, 1H), 8.31 (s, 1H), 8.16 (d, J=8.8 Hz, 1H), 7.90 (dd, J=1.9, 8.8 Hz, 1H), 7.65 (q, J=4.2 Hz, 1H) and 5.69 (s, 2H) ppm.

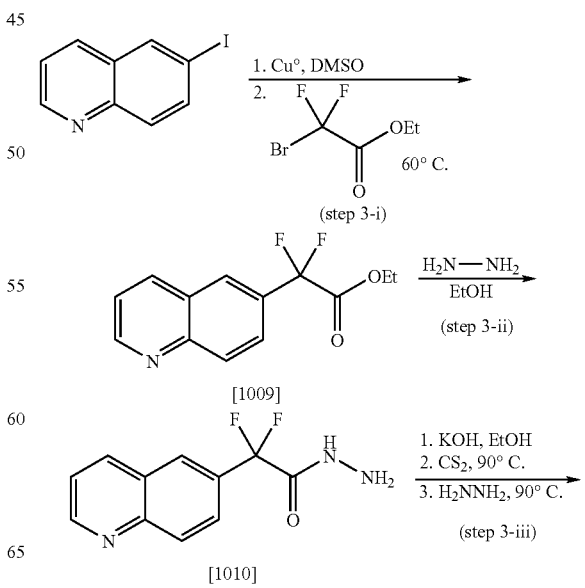

-continued

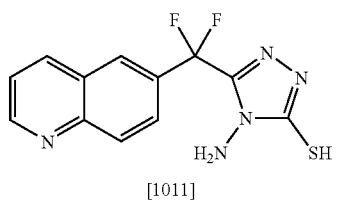

[1011]

Example 4

Compounds of Formula IV

Compounds 1012 and 1016 were purchased from Ryan Scientific Co. (Catalog Nos. B021891 and 11M-321S, respectively). Compounds 1013 and 1014 were purchased from Princeton Biomolecular Research (Catalog Nos. PBMR 006134 and PBMR 019329, respectively). Compound 1015 was purchased from UkrOrgSynthesis (Catalog No. BBV-2081906).

Compounds of Formula IV

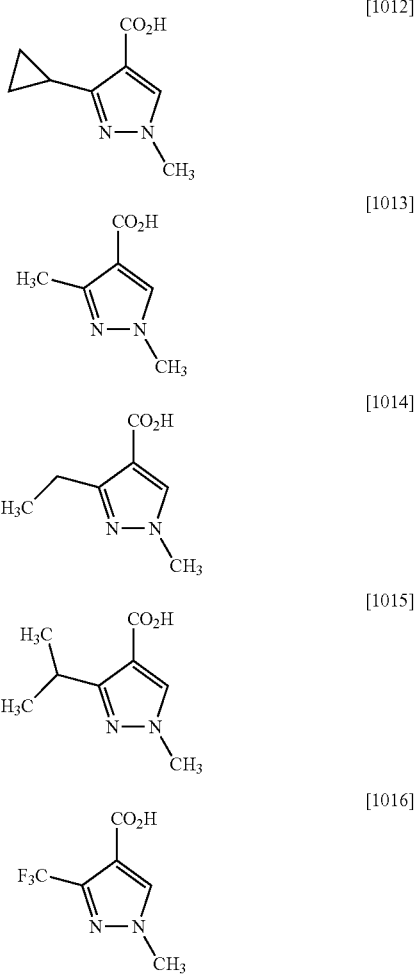

[1012]

[1013]

[1014]

[1015]

[1016]

Example 5

Preparation of Compounds of Formula I

As shown in step 5-i of Scheme 5, a compound of formula III (453.3 mmol, 1.00 equivalent) and a compound of formula IV (476.0 mmol, 1.05 equivalents) are dissolved in $POCl_3$ (1.23 liters) and sulfolane (246 mL). The resulting mixture is stirred for 18 hours at 83° C. The volatiles are evaporated under reduced pressure and the residue additionally azeotroped with toluene twice more under reduced pressure. The resulting oil is slowly poured into stirring ice-water and the aqueous solution is extracted with dichloromethane to remove any residual sulfolane. The aqueous solution is treated with saturated sodium bicarbonate (3.2 liters) until a pH of 7 is achieved. The resulting oil is decanted off and dissolved in a small amount of methanol, with the remaining aqueous layer extracted with dichloromethane (4 times). The combined organic extracts and the methanol solution of the oil are combined and washed with saturated sodium bicarbonate, water, and brine, respectively. The organics are dried over anhydrous $MgSO_4$, filtered, and evaporated under reduced pressure to afford the crude product as a thick brown oil. The product is purified by silica gel chromatography, eluting with a gradient of dichloromethane to 5% methanol in dichloromethane. Fractions containing product are evaporated under reduced pressure to provide compounds of formula I, which can be further purified by crystallization from dichloromethane and methyl t-butyl ether. Racemic mixtures of compounds can be separated into their respective enantiomers by supercritical fluid chromatography using a ChiralPak® AD-H column (20 mm×250 mm, 5 micron column) or a ChiralCel® OJ-H column (20 mm×250 mm, 5 micron column), eluting with an appropriate MeOH (0.1% DEA)/$CO_2$ ratio at an appropriate flow rate. Analytical data for compounds of the invention are shown in Table 1.

Scheme 5

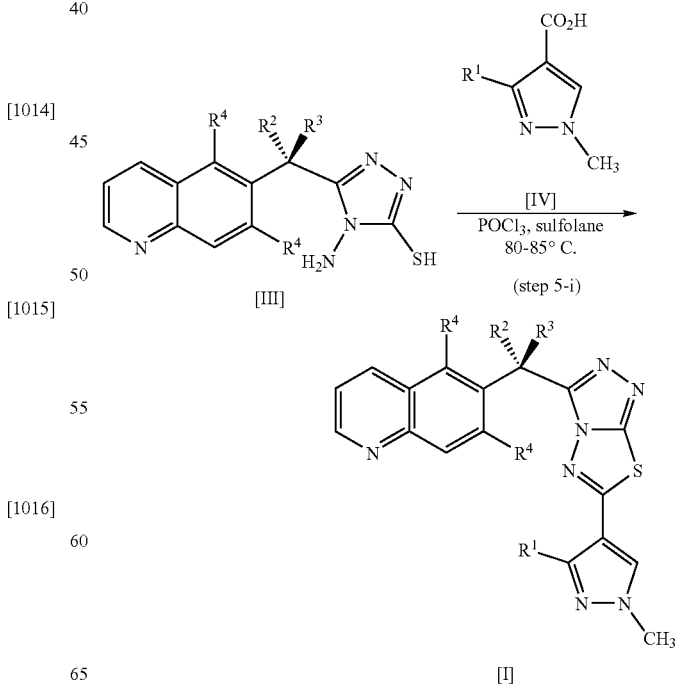

TABLE 1

| | | $^1$H NMR (300 MHz, unless indicated otherwise), |
|---|---|---|
| Cmpd. No. | ESMS (M + H) | NMR peaks given as δ values |
| 1 | 362.00 | (DMSO-d$_6$) δ 9.17 (dd, J = 1.4, 4.9 Hz, H), 8.93 (d, J = 8.3 Hz, H), 8.48 (s, H), 8.29-8.24 (m, 2H), 8.08 (dd, J = 1.8, 8.8 Hz, H), 7.93 (dd, J = 5.0, 8.4 Hz, H), 4.73 (s, 2H), 3.82 (s, 3H) and 2.30 (s, 3H) ppm |
| 2 | 376.00 | (DMSO-d$_6$) δ 9.19 (dd, J = 1.4, 5.0 Hz, H), 8.97 (d, J = 8.3 Hz, H), 8.48 (s, H), 8.31 (d, J = 8.8 Hz, H), 8.25 (s, H), 8.08 (dd, J = 1.8, 8.8 Hz, H), 7.96 (dd, J = 5.0, 8.4 Hz, H), 4.74 (s, 2H), 3.83 (s, 3H), 2.68 (q, J = 7.5 Hz, 2H) and 1.05 (t, J = 7.5 Hz, 3H) ppm |
| 3 | 416.00 | (DMSO-d$_6$) δ 9.21 (dd, J = 1.4, 5.1 Hz, H), 8.97 (d, J = 8.2 Hz, H), 8.85 (s, H), 8.31 (d, J = 8.8 Hz, H), 8.24 (s, H), 8.09 (dd, J = 1.8, 8.8 Hz, H), 7.99 (dd, J = 5.1, 8.4 Hz, H), 4.74 (s, 2H) and 3.99 (s, 3H) ppm |
| 4 | 390.00 | (DMSO-d$_6$) δ 9.17 (dd, J = 1.4, 4.9 Hz, H), 8.92 (d, J = 8.2 Hz, H), 8.45 (s, H), 8.28-8.22 (m, 2H), 8.03 (dd, J = 1.8, 8.8 Hz, H), 7.94 (dd, J = 4.9, 8.4 Hz, H), 4.73 (s, 2H), 3.82 (s, 3H), 3.13 (qn, J = 6.8 Hz, H) and 1.07-1.01 (m, 6H) ppm |
| 5 | 376.00 | (DMSO-d$_6$) δ 9.20 (d, J = 5.0 Hz, H), 9.01 (d, J = 8.3 Hz, H), 8.45 (s, H), 8.31 (d, J = 9.1 Hz, 2H), 8.14-8.10 (m, H), 7.98 (dd, J = 5.1, 8.3 Hz, H), 5.00 (q, J = 7.2 Hz, H), 3.80 (s, 3H), 2.23 (s, 3H) and 1.91 (d, J = 7.2 Hz, 3H) ppm |
| 6 | 430.00 | (DMSO-d$_6$) δ 9.12 (dd, J = 1.3, 4.8 Hz, H), 8.81 (d, J = 7.3 Hz, 2H), 8.18 (d, J = 8.8 Hz, 2H), 8.00 (dd, J = 1.6, 8.9 Hz, H), 7.86 (dd, J = 4.9, 8.3 Hz, H), 4.97 (q, J = 7.1 Hz, H), 3.97 (s, 3H) and 1.90 (d, J = 7.2 Hz, 3H) ppm |
| 7 | 390.00 | (DMSO-d$_6$) δ 9.20-9.18 (m, H), 8.99 (d, J = 8.3 Hz, H), 8.46 (d, J = 8.5 Hz, H), 8.31-8.27 (m, 2H), 8.07 (dd, J = 1.7, 8.8 Hz, H), 7.97 (dd, J = 5.1, 8.4 Hz, H), 5.01 (q, J = 7.0 Hz, H), 3.75 (s, 3H), 2.61-2.50 (m, 2H), 1.90 (d, J = 7.1 Hz, 3H) and 0.97 (t, J = 7.5 Hz, 3H) ppm |
| 8 | 402.00 | (DMSO-d$_6$) δ d 9.21 (dd, J = 1.3, 5.0 Hz, H), 9.01 (d, J = 8.2 Hz, H), 8.40 (s, H), 8.33-8.29 (m, 2H), 8.09 (dd, J = 1.8, 8.8 Hz, H), 7.99 (dd, J = 5.1, 8.4 Hz, H), 5.00 (q, J = 7.1 Hz, H), 3.76 (s, 3H), 2.00-1.88 (m, 4H) and 0.84-0.58 (m, 4H) ppm |
| 9 | 376.00 | (DMSO-d$_6$) δ 9.20 (d, J = 5.0 Hz, H), 9.01 (d, J = 8.3 Hz, H), 8.45 (s, H), 8.31 (d, J = 9.1 Hz, 2H), 8.14-8.10 (m, H), 7.98 (dd, J = 5.1, 8.3 Hz, H), 5.00 (q, J = 7.2 Hz, H), 3.80 (s, 3H), 2.23 (s, 3H) and 1.91 (d, J = 7.2 Hz, 3H) ppm |
| 10 | 390.00 | (DMSO-d$_6$) δ 9.20-9.18 (m, H), 8.99 (d, J = 8.3 Hz, H), 8.46 (d, J = 8.5 Hz, H), 8.31-8.27 (m, 2H), 8.07 (dd, J = 1.7, 8.8 Hz, H), 7.97 (dd, J = 5.1, 8.4 Hz, H), 5.01 (q, J = 7.0 Hz, H), 3.75 (s, 3H), 2.61-2.50 (m, 2H), 1.90 (d, J = 7.1 Hz, 3H) and 0.97 (t, J = 7.5 Hz, 3H) ppm |
| 11 | 430.00 | (DMSO-d$_6$) δ 9.12 (dd, J = 1.3, 4.8 Hz, H), 8.81 (d, J = 7.3 Hz, 2H), 8.18 (d, J = 8.8 Hz, 2H), 8.00 (dd, J = 1.6, 8.9 Hz, H), 7.86 (dd, J = 4.9, 8.3 Hz, H), 4.97 (q, J = 7.1 Hz, H), 3.97 (s, 3H) and 1.90 (d, J = 7.2 Hz, 3H) ppm |
| 12 | 402.00 | (DMSO-d$_6$) δ 9.21 (dd, J = 1.3, 5.0 Hz, H), 9.01 (d, J = 8.2 Hz, H), 8.40 (s, H), 8.33-8.29 (m, 2H), 8.09 (dd, J = 1.8, 8.8 Hz, H), 7.99 (dd, J = 5.1, 8.4 Hz, H), 5.00 (q, J = 7.1 Hz, H), 3.76 (s, 3H), 2.00-1.88 (m, 4H) and 0.84-0.58 (m, 4H) ppm |
| 13 | 390.00 | (DMSO-d$_6$) δ 9.16 (dd, J = 1.4, 4.9 Hz, H), 8.97 (d, J = 8.3 Hz, H), 8.40 (s, H), 8.28 (d, J = 1.9 Hz, H), 8.21 (d, J = 9.0 Hz, H), 7.97-7.91 (m, 2H), 3.78 (d, J = 11.9 Hz, 3H) and 2.01 (d, J = 1.6 Hz, 9H) ppm |
| 14 | 398.00 | (DMSO-d$_6$) δ 9.03 (dd, J = 1.5, 4.4 Hz, H), 8.56 (d, J = 7.8 Hz, H), 8.46 (s, H), 7.77 (d, J = 10.8 Hz, H), 7.67 (q, J = 4.3 Hz, H), 4.68 (s, 2H), 3.81 (s, 3H) and 2.18 (s, 3H) ppm |

TABLE 1-continued

Physical Characterization of Compounds of Formula I

| Cmpd. No. | ESMS (M + H) | $^1$H NMR (300 MHz, unless indicated otherwise), NMR peaks given as δ values |
|---|---|---|
| 15 | 412.00 | (DMSO-$d_6$) δ 9.03 (dd, J = 1.5, 4.3 Hz, H), 8.55 (d, J = 8.4 Hz, H), 8.46 (s, H), 7.76 (d, J = 10.8 Hz, H), 7.67 (q, J = 4.3 Hz, H), 4.68 (s, 2H), 3.79 (d, J = 10.9 Hz, 3H), 2.61-2.52 (m, 2H) and 0.99 (t, J = 7.5 Hz, 3H) ppm |
| 16 | 426.00 | (DMSO-$d_6$) δ 9.02 (dd, J = 1.5, 4.2 Hz, H), 8.55-8.53 (m, H), 8.43 (s, H), 7.76-7.65 (m, 2H), 4.69 (s, 2H), 3.80 (s, 3H), 3.02 (qn, J = 6.9 Hz, H) and 1.00-0.96 (m, 6H) ppm |
| 17 | 452.00 | (DMSO-$d_6$) δ 9.02 (dd, J = 1.5, 4.3 Hz, H), 8.81 (s, H), 8.52 (d, J = 7.7 Hz, H), 7.74-7.64 (m, 2H), 4.67 (s, 2H) and 3.96 (s, 3H) ppm |
| 18 | 412.00 | (DMSO-$d_6$) δ 9.04-9.02 (m, H), 8.55 (d, J = 8.4 Hz, H), 8.42 (s, H), 7.75 (d, J = 11.6 Hz, H), 7.67 (q, J = 4.3 Hz, H), 5.18 (q, J = 7.0 Hz, H), 3.75 (d, J = 4.9 Hz, 3H) and 1.97-1.90 (m, 6H) ppm |
| 19 | 412.00 | (DMSO-$d_6$) δ 9.04-9.02 (m, H), 8.55 (d, J = 8.4 Hz, H), 8.42 (s, H), 7.75 (d, J = 11.6 Hz, H), 7.67 (q, J = 4.3 Hz, H), 5.18 (q, J = 7.0 Hz, H), 3.75 (d, J = 4.9 Hz, 3H) and 1.97-1.90 (m, 6H) ppm |
| 20 | 398.00 | (DMSO-$d_6$) δ 9.06 (dd, J = 1.6, 4.2 Hz, H), 8.59 (d, J = 11.1 Hz, 2H), 8.48 (s, H), 8.21 (d, J = 8.8 Hz, H), 8.02 (dd, J = 2.0, 8.9 Hz, H), 7.68 (q, J = 4.2 Hz, 1H), 3.83 (s, 3H) and 2.27 (s, 3H) ppm |
| 21 | 426.00 | (DMSO-$d_6$) δ 9.22 (dd, J = 1.4, 4.6 Hz, H), 8.88 (d, J = 8.1 Hz, H), 8.63 (s, H), 8.55 (s, H), 8.35 (d, J = 8.9 Hz, H), 8.14 (dd, J = 1.9, 8.9 Hz, H), 7.90 (dd, J = 4.6, 8.4 Hz, H), 3.83 (s, 3H), 3.04 (qn, J = 6.8 Hz, H) and 1.05-1.02 (m, 6H) ppm |

Biological assay of Compounds of Formula I

Example 2 c-Met Kinase Inhibition Assay

The compounds of the invention were screened for their ability to inhibit c-Met kinase using a standard radiometric assay. Briefly, in this kinase assay the transfer of the terminal $^{33}$P-phosphate in $^{33}$P-ATP to substrate polyE4Y is interrogated. The assay was carried out in 96-well plates to a final volume of 100 μL per well containing 0.5 nM c-Met, 100 mM HEPES (pH 7.5), 10 mM $MgCl_2$, 25 mM NaCl, 0.01% BSA, 1 mM DTT, 0.5 mg/mL polyE4Y, and 35 μM ATP. Accordingly, compounds of the invention were dissolved in DMSO to make 10 mM initial stock solutions. Serial dilutions in DMSO were then made to obtain the final solutions for the assay. A 1.5 μL aliquot of DMSO or inhibitor in DMSO was added to each well, followed by the addition of $^{33}$P-ATP, and finally the addition of c-Met and polyE4Y (obtained from Sigma). After 20 min, the reaction was quenched with 50 μL of 30% trichloroacetic acid (TCA) containing 4 mM ATP. The reaction mixture was transferred to the 0.66 mm GF filter plates (Corning) and washed three times with 5% TCA. Following the addition of 50 μL of Ultimate Gold™ high efficiency scintillant (Packard Bioscience), the samples were counted in a Packard TopCount NXT Microplate Scintillation and Luminescence Counter (Packard BioScience). The $K_i$ values, shown in Table 2, were calculated using Microsoft Excel Solver macros to fit the data to the kinetic model for competitive tight-binding inhibition.

Example 3

Inhibition c-Met Activity in Snu5 Gastric Carcinoma Cells

Compounds of formula I were also screened for their ability to inhibit the Luciferase-induced signal in an engineered Snu5 cell line. Snu5 [obtained from American Type Culture Collection (Catalog number CRL-5973)] is a human gastric carcinoma known to overexpress c-Met, which is constitutively active. The cell line was transduced with the retrovirus, pCLPCX, which contains a genetic construct consisting of 6×AP1 promoter response elements and a luciferase gene having a C-terminal PEST sequence (proteolytic signal from mouse ornithine decarboxylase, which reduces the half-life of the luciferase). The constitutively active c-Met activates cellular pathways (principally MAP kinase), resulting in AP-1-induced transcription of luciferase-PEST and translation into the final product, the activity of which is quantifiable as a chemiluminescent readout upon the addition of luciferin (Steady-Glo from Promega.). Residual luminescence is strongly correlated to the inhibition of c-Met. A stable cell line was obtained by selecting the new cell line (Snu5-AP1-Luc-Pest) with puromycin. The cells were grown in complete media [Iscove's media (Invitrogen) containing 10% fetal bovine serum (FBS, Hyclone) and penicillin/gentamycin (Invitrogen)]. Compounds of the invention were dissolved in DMSO to make 10 mM initial stock solutions. Serial dilutions in DMSO were then made and transferred to complete medium to make a 10× solution. The Snu5-AP1-Luc-Pest cells were counted and diluted to 200,000-cells/mL solution. The cells (90 μL) were added to each well in a 96-well black with clear bottom plate (Costar). Then 10 μL of the 10× compound solution was added to the cells in triplicate. The plates were incubated in a 37° C./5% $CO_2$ incubator. After 6 hours, 50 μL of the Steady-Glo reagent (Promega) was added to each well and placed on a plate shaker for 5 minutes to ensure that the cells were completely lysed. The plate was read on a 1450 Microbeta Liquid Scintillation and Luminescence Counter (Perkin-Elmer). The $IC_{50}$ values, shown in Table 2, were calculated using a 4-parameter fit using the graphing software Prism (GraphPad).

TABLE 2

Comparative c-Met receptor binding and SNU5 activity values for compounds of Formula I

| $R^1$ | H— | $CH_3$— | $CF_3$— | $CH_3CH_2$— | $(CH_3)_2CH$— | 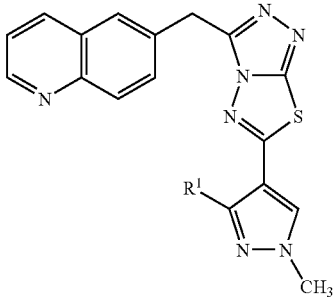 |
|---|---|---|---|---|---|---|

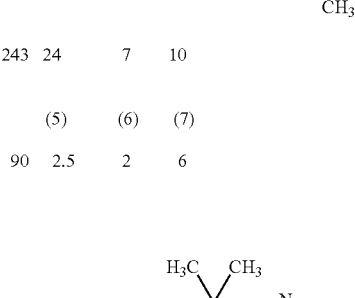

| | | | | | | |
|---|---|---|---|---|---|---|
| c-Met $K_i$ (nM) | 36 | 6 | 2.5 | 3 | 5 | |
| Cmpd. No. | | (1) | (3) | (2) | (4) | |
| SNU5-AP1 $IC_{50}$ (nM) | 85 | 2 | 2 | 4 | 3 | |

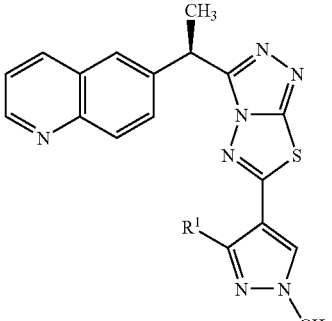

| | | | | | | |
|---|---|---|---|---|---|---|
| c-Met $K_i$ (nM) | 24 | 15 | 3 | 5 | | 7 |
| Cmpd. No. | | (9) | (11) | (10) | | (12) |
| SNU5-AP1 $IC_{50}$ (nM) | 15 | 3 | 2 | 6.2 | | 7 |

TABLE 2-continued

Comparative c-Met receptor binding and SNU5 activity values for compounds of Formula I

| $R^1$ | H— | $CH_3$— | $CF_3$— | $CH_3CH_2$— | $(CH_3)_2CH$— | 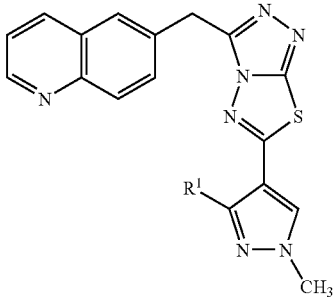 |
|---|---|---|---|---|---|---|

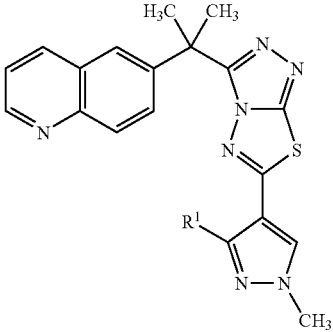

| | | | | | | |
|---|---|---|---|---|---|---|
| c-Met $K_i$ (nM) | 243 | 24 | 7 | 10 | | 24 |
| Cmpd. No. | | (5) | (6) | (7) | | (8) |
| SNU5-AP1 $IC_{50}$ (nM) | 90 | 2.5 | 2 | 6 | | 3 |

| | | | | | | |
|---|---|---|---|---|---|---|
| c-Met $K_i$ (nM) | 3400 | 360 | | | | |
| Cmpd. No. | | (13) | | | | |
| SNU5-AP1 $IC_{50}$ (nM) | >1000 | 250 | | | | |

| | | | | | | |
|---|---|---|---|---|---|---|
| c-Met $K_i$ (nM) | 16 | 7 | 2 | 2.5 | 2.4 | |

TABLE 2-continued

Comparative c-Met receptor binding and SNU5 activity values for compounds of Formula I

| $R^1$ | H— | $CH_3$— | $CF_3$— | $CH_3CH_2$— | $(CH_3)_2CH$— | cyclopropyl |
|---|---|---|---|---|---|---|
| Cmpd. No. | | (14) | (17) | (15) | (16) | |
| SNU5-AP1 $IC_{50}$ (nM) | | 12 | 2 | 2.5 | 2 | 3 |

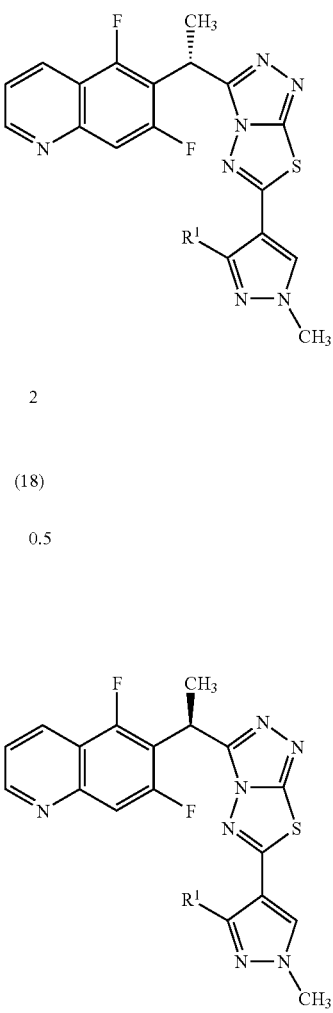

| c-Met Ki (nM) | | 5 | 2 | | | |
| Cmpd. No. | | | (18) | | | |
| SNU5-AP1 $IC_{50}$ (nM) | | 6 | 0.5 | | | |

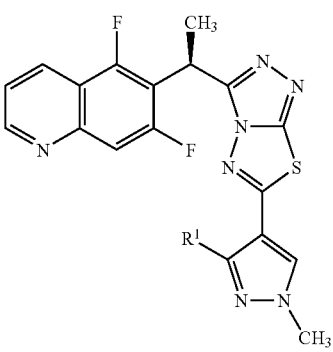

| c-Met Ki (nM) | | 70 | 22 | | | |
| Cmpd. No. | | | (19) | | | |
| SNU5-AP1 $IC_{50}$ (nM) | | 60 | 5 | | | |

TABLE 2-continued

Comparative c-Met receptor binding and SNU5 activity values for compounds of Formula I

| $R^1$ | H— | $CH_3$— | $CF_3$— | $CH_3CH_2$— | $(CH_3)_2CH$— | cyclopropyl |
|---|---|---|---|---|---|---|

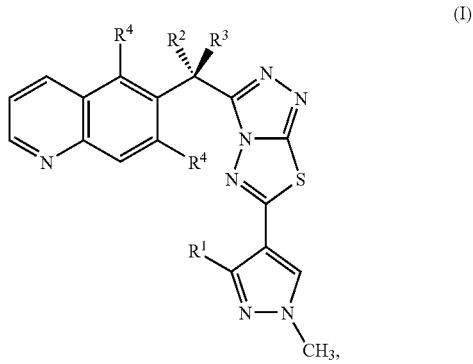

| c-Met Ki (nM) | | 36 | 14 | | | 4 |
| Cmpd. No. | | (20) | | | | (21) |
| SNU5-AP1 $IC_{50}$ (nM) | | 14 | 4 | | | 6 |

All publications and patents cited in this specification are herein incorporated by reference as if each individual publication or patent were specifically and individually indicated to be incorporated by reference. Although the foregoing invention has been described in some detail by way of illustration and example for purposes of clarity or understanding, it will be readily apparent to those of ordinary skill in the art in light of the teachings of this invention that certain changes and modifications may be made thereto without departing from the spirit or scope of the appended claims.

What is claimed is:

1. A compound having the formula:

(I)

or a pharmaceutically acceptable salt thereof, wherein
$R^1$ is cyclopropyl or $C_{1-3}$ aliphatic, optionally substituted with 1-3 fluorine atoms;
$R^2$ is hydrogen, fluoro, or methyl;
$R^3$ is hydrogen, fluoro, or methyl; and
$R^4$ is hydrogen or fluoro.

2. The compound according to claim 1, wherein $R^1$ is methyl, ethyl, trifluoromethyl, isopropyl, or cyclopropyl; $R^2$ is hydrogen or methyl; $R^3$ is hydrogen or methyl; and $R^4$ is hydrogen or fluoro.

3. The compound according to claim 1, wherein $R^1$ is methyl, ethyl, trifluoromethyl, isopropyl, or cyclopropyl; each of $R^2$ and $R^3$ is fluoro; and $R^4$ is hydrogen.

4. The compound according to claim 1, wherein $R^1$ is methyl.

5. The compound according to claim 1, wherein $R^1$ is ethyl, trifluoromethyl, isopropyl, or cyclopropyl.

6. The compound according to claim 1, wherein $R^2$ is hydrogen and $R^3$ is methyl.

7. The compound according to claim 1, wherein $R^2$ is methyl and $R^3$ is hydrogen.

8. The compound according to claim 1, wherein each of $R^2$ and $R^3$ is hydrogen.

9. The compound according to claim 1, wherein each of $R^2$ and $R^3$ is fluoro.

10. The compound according to any one of claims 4 to 8, wherein each of $R^4$ is fluorine.

11. The compound according to any one of claims 4 to 9, wherein each of $R^4$ is hydrogen.

12. The compound according to claim 1 having the following structue:

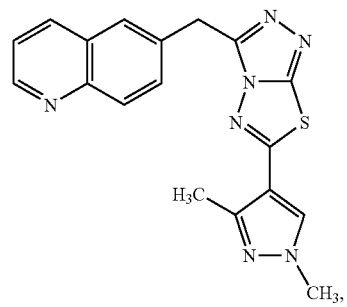

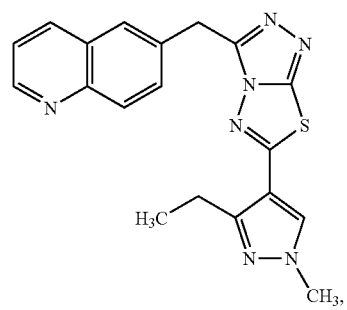

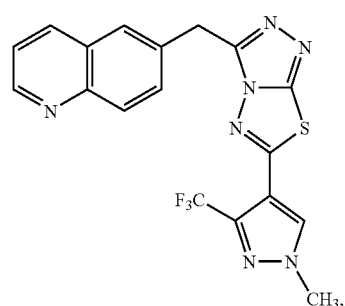

-continued

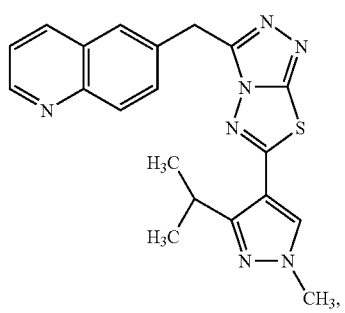

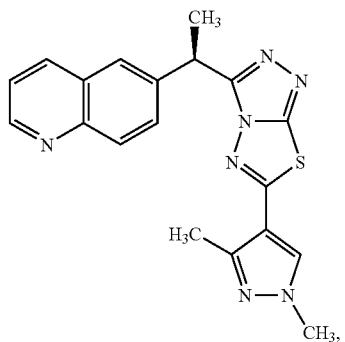

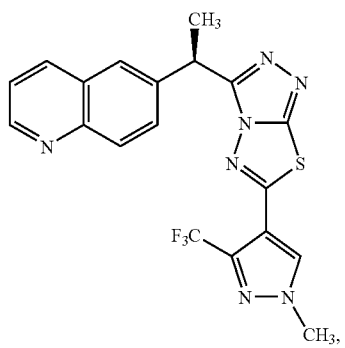

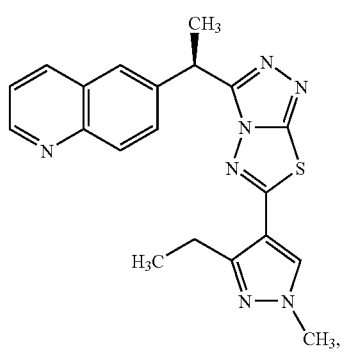

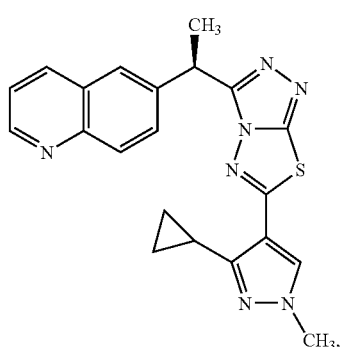

-continued
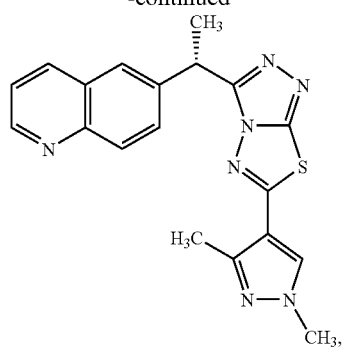
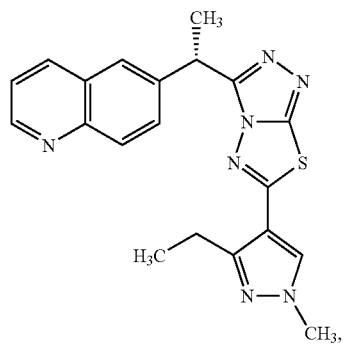
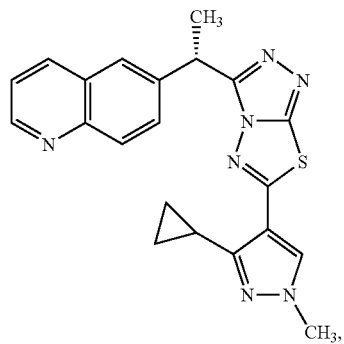
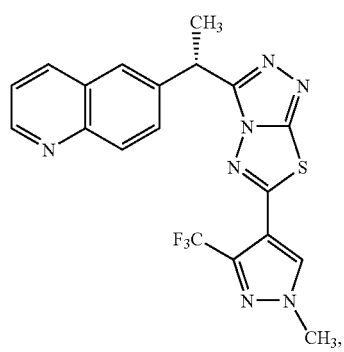
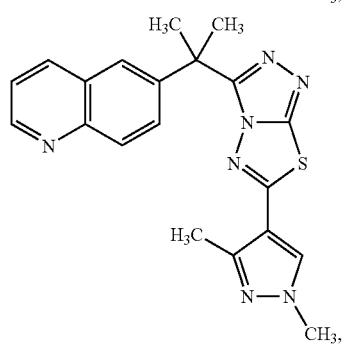
-continued
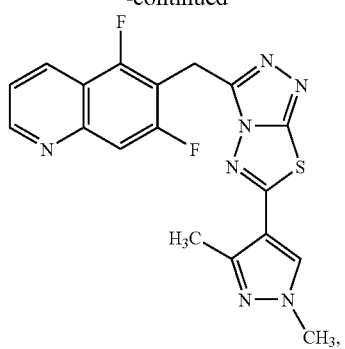
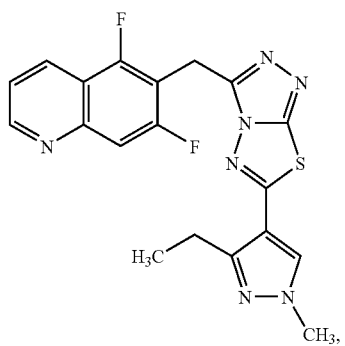
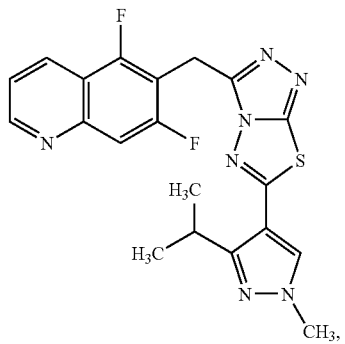
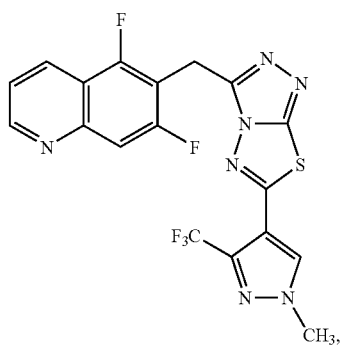
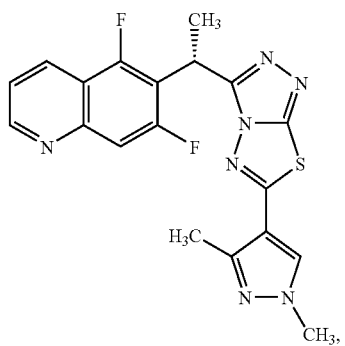

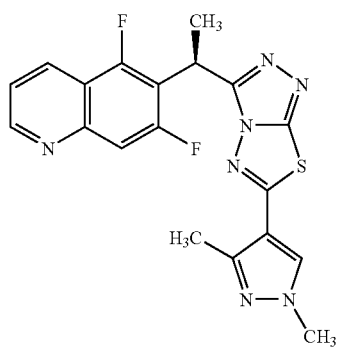

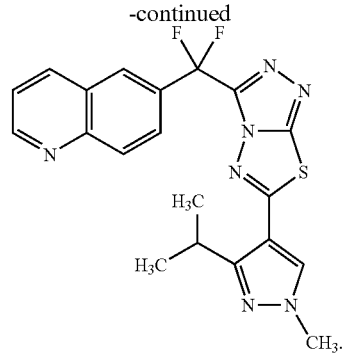

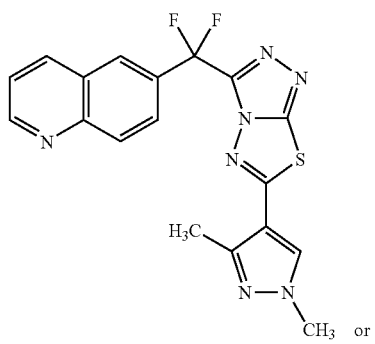

or

13. A pharmaceutical composition comprising a compound according to any one of claim 1 to 9 or 12, or a pharmaceutically acceptable salt thereof, and a pharmaceutically acceptable carrier, adjuvant or vehicle.

14. The composition according to claim 13, additionally comprising a chemotherapeutic or anti-proliferative agent, an anti-inflammatory agent, an agent for treating atherosclerosis, or an agent for treating lung fibrosis.

15. A method of treating or lessening the severity of a proliferative disorder in a patient comprising administering the compound according to claim 1, or a pharmaceutical composition comprising said compound, in an amount sufficient to treat or lessen the severity of said proliferative disorder in said patient.

16. The method according to claim 15, wherein said disorder is metastatic cancer.

17. The method according to claim 15, wherein said disorder is a glioblastoma; a gastric carcinoma; or a cancer selected from colon, breast, prostate, brain, liver, pancreatic or lung cancer.

18. The method according to claim 15, wherein said disorder is hepatocellular carcinoma.

* * * * *